US012667696B2

(12) United States Patent
Brenizer et al.

(10) Patent No.: US 12,667,696 B2
(45) Date of Patent: Jun. 30, 2026

(54) GUIDE EXTENSION CATHETER

(71) Applicant: Teleflex Life Sciences LLC,
Wilmington, DE (US)

(72) Inventors: Joshua Brenizer, Oak Grove, MN
(US); Dean Peterson, Minneapolis, MN
(US); Mark Wendle, Albany, NY (US)

(73) Assignee: Teleflex Life Sciences LLC,
Wilmington, DE (US)

( * ) Notice: Subject to any disclaimer, the term of this
patent is extended or adjusted under 35
U.S.C. 154(b) by 0 days.

(21) Appl. No.: 18/581,812

(22) Filed: Feb. 20, 2024

(65) Prior Publication Data

US 2024/0189547 A1      Jun. 13, 2024

Related U.S. Application Data

(60) Division of application No. 17/843,687, filed on Jun.
17, 2022, now abandoned, which is a continuation of
(Continued)

(51) Int. Cl.
A61M 25/01      (2006.01)
A61M 25/00      (2006.01)
A61M 25/06      (2006.01)

(52) U.S. Cl.
CPC .... A61M 25/0113 (2013.01); A61M 25/0023
(2013.01); A61M 25/0053 (2013.01);
(Continued)

(58) Field of Classification Search
CPC .............. A61M 25/01; A61M 25/0662; A61M
25/0023; A61M 2025/0004; A61M
25/0113
See application file for complete search history.

(56) References Cited

U.S. PATENT DOCUMENTS

| | | | |
|---|---|---|---|
| 4,000,739 A | 1/1977 | Stevens |
| 4,166,468 A | 9/1979 | Haynie |

(Continued)

FOREIGN PATENT DOCUMENTS

| | | |
|---|---|---|
| CA | 2008784 C | 7/2002 |
| DE | 69928825 | 7/2006 |

(Continued)

OTHER PUBLICATIONS

Alegria, Jorge R; Holmes, David; and Topol, Eric J. "Textbook of
Interventional Cardiology," Saunders Elseveir, 5th Edition, 2008, p.
277-280.

(Continued)

*Primary Examiner* — Emily L Schmidt
(74) *Attorney, Agent, or Firm* — Dorsey & Whitney LLP

(57)      ABSTRACT

A guide extension catheter can comprise an elongate tube
member, a push member, and a concave track. The elongate
tube member can define a lumen and three distinct portions
of different diameter. A distal portion can define a first
diameter, a proximal portion can define a second diameter
which is larger than the first diameter but smaller than a
lumen of a guide catheter with which the guide extension
catheter is used, and a tapered portion, positioned between
the distal portion and the proximal portion, can have a
variable diameter. The push member can be eccentrically
coupled relative to the tube member and extends proximally
therefrom for slidably positioning the tube member within
and partially beyond a distal end of the guide catheter. The
concave track forms a transition between the tube member
and the push member, and defines a partially cylindrical
opening leading into the tube member.

16 Claims, 7 Drawing Sheets

Related U.S. Application Data application No. 16/264,803, filed on Feb. 1, 2019, now abandoned.

(60) Provisional application No. 62/630,321, filed on Feb. 14, 2018.

(52) U.S. Cl.
CPC . *A61M 25/0662* (2013.01); *A61M 2025/0004* (2013.01); *A61M 25/0009* (2013.01); *A61M 25/0012* (2013.01)

(56) References Cited

U.S. PATENT DOCUMENTS

| | | | |
|---|---|---|---|
| 4,289,128 A | 9/1981 | Rusch |
| 4,723,936 A | 2/1988 | Buchbinder et al. |
| 4,762,129 A | 8/1988 | Bonzel |
| 4,813,930 A | 3/1989 | Elliott |
| 4,832,028 A | 5/1989 | Patel |
| 4,838,268 A | 6/1989 | Keith et al. |
| 4,838,269 A | 6/1989 | Robinson et al. |
| 4,909,252 A | 3/1990 | Goldberger |
| 4,921,483 A | 5/1990 | Wijay et al. |
| 4,932,413 A | 6/1990 | Shockey et al. |
| 4,943,278 A | 7/1990 | Euteneuer et al. |
| 4,946,440 A | 8/1990 | Hall |
| 4,994,745 A | 2/1991 | Mizuta |
| 5,002,531 A | 3/1991 | Bonzel |
| 5,040,548 A | 8/1991 | Yock |
| 5,061,273 A | 10/1991 | Yock |
| 5,074,845 A | 12/1991 | Miraki et al. |
| 5,098,412 A | 3/1992 | Shiu |
| 5,102,403 A | 4/1992 | Alt |
| 5,120,323 A | 6/1992 | Shockey et al. |
| 5,122,125 A | 6/1992 | Deuss |
| 5,156,594 A | 10/1992 | Keith |
| 5,232,445 A | 8/1993 | Bonzel |
| 5,234,416 A | 8/1993 | Macaulay et al. |
| 5,257,974 A | 11/1993 | Cox |
| 5,267,958 A | 12/1993 | Buchbinder et al. |
| 5,290,247 A | 3/1994 | Crittenden |
| 5,328,472 A | 7/1994 | Steinke et al. |
| 5,350,395 A | 9/1994 | Yock |
| 5,368,567 A | 11/1994 | Lee |
| 5,383,853 A | 1/1995 | Jung et al. |
| 5,413,560 A | 5/1995 | Solar |
| 5,415,639 A | 5/1995 | VandenEinde et al. |
| 5,439,445 A | 8/1995 | Kontos |
| 5,441,489 A | 8/1995 | Utsumi et al. |
| 5,445,624 A | 8/1995 | Jimenez |
| 5,445,625 A | 8/1995 | Voda |
| 5,451,209 A | 9/1995 | Ainsworth et al. |
| 5,472,425 A | 12/1995 | Teirstein |
| 5,489,278 A | 2/1996 | Abrahamson |
| 5,527,292 A | 6/1996 | Adams et al. |
| 5,531,721 A | 7/1996 | Pepin et al. |
| 5,545,149 A | 8/1996 | Brin et al. |
| 5,549,553 A | 8/1996 | Ressemann et al. |
| 5,562,620 A | 10/1996 | Klein et al. |
| 5,567,203 A | 10/1996 | Euteneuer et al. |
| 5,571,087 A | 11/1996 | Ressemann et al. |
| 5,578,009 A | 11/1996 | Kraus et al. |
| 5,599,326 A | 2/1997 | Carter |
| 5,620,417 A | 4/1997 | Jang et al. |
| 5,649,909 A | 7/1997 | Cornelius |
| 5,658,263 A | 8/1997 | Dang et al. |
| 5,690,613 A | 11/1997 | Verbeek |
| 5,704,926 A | 1/1998 | Sutton |
| 5,720,300 A | 2/1998 | Fagan et al. |
| 5,720,724 A | 2/1998 | Ressemann et al. |
| 5,743,876 A | 4/1998 | Swanson |
| 5,755,704 A | 5/1998 | Lunn |
| 5,772,642 A | 6/1998 | Ciamacco et al. |
| 5,776,141 A | 7/1998 | Klein et al. |
| 5,785,685 A | 7/1998 | Kugler et al. |
| 5,792,124 A | 8/1998 | Horrigan et al. |
| 5,843,022 A | 12/1998 | Willard et al. |
| 5,860,963 A | 1/1999 | Azam et al. |
| 5,891,056 A | 4/1999 | Ramzipoor |
| 5,902,290 A | 5/1999 | Peacock, I et al. |
| 5,911,715 A | 6/1999 | Berg et al. |
| 5,961,510 A | 10/1999 | Fugoso et al. |
| 5,980,486 A | 11/1999 | Enger |
| 6,042,578 A | 3/2000 | Dinh et al. |
| 6,071,273 A | 6/2000 | Euteneuer et al. |
| 6,159,195 A | 12/2000 | Ha et al. |
| 6,190,358 B1 | 2/2001 | Fitzmaurice et al. |
| 6,193,686 B1 | 2/2001 | Estrada et al. |
| 6,199,262 B1 | 3/2001 | Martin |
| 6,245,053 B1 | 6/2001 | Benjamin |
| 6,270,465 B1 | 8/2001 | Keith et al. |
| 6,299,628 B1 | 10/2001 | Harrison et al. |
| 6,338,725 B1 | 1/2002 | Hermann et al. |
| 6,398,773 B1 | 6/2002 | Bagaoisan et al. |
| 6,409,863 B1 | 6/2002 | Williams et al. |
| 6,443,912 B1 | 9/2002 | Mazzola et al. |
| 6,475,195 B1 | 11/2002 | Voda |
| 6,488,655 B1 | 12/2002 | Wantink et al. |
| 6,503,223 B1 | 1/2003 | Sekido et al. |
| 6,503,353 B1 | 1/2003 | Peterson et al. |
| 6,548,010 B1 | 4/2003 | Stivland et al. |
| 6,575,958 B1 | 6/2003 | Happ et al. |
| 6,591,472 B1 | 7/2003 | Noone et al. |
| 6,595,952 B2 | 7/2003 | Forsberg |
| 6,610,068 B1 | 8/2003 | Yang |
| 6,620,149 B1 | 9/2003 | Lenz et al. |
| 6,626,889 B1 | 9/2003 | Simpson et al. |
| 6,635,029 B1 | 10/2003 | Venturelli |
| 6,638,268 B2 | 10/2003 | Niazi |
| 6,648,874 B2 | 11/2003 | Parisi et al. |
| 6,689,144 B2 | 2/2004 | Gerberding |
| 6,706,018 B2 | 3/2004 | Westlund et al. |
| 6,733,487 B2 | 5/2004 | Keith et al. |
| 6,755,812 B2 | 6/2004 | Peterson et al. |
| 6,761,696 B1 | 7/2004 | Wong |
| 6,837,890 B1 | 1/2005 | Chludzinski et al. |
| 6,860,876 B2 | 3/2005 | Chen |
| 6,997,908 B2 | 2/2006 | Carrillo, Jr. et al. |
| 7,169,162 B2 | 1/2007 | Garakani |
| 7,232,452 B2 | 6/2007 | Adams et al. |
| 7,294,124 B2 | 11/2007 | Eidenschink |
| 7,374,560 B2 | 5/2008 | Ressemann et al. |
| 7,422,579 B2 | 9/2008 | Wahr et al. |
| 7,544,201 B2 | 6/2009 | Pepper |
| 7,604,612 B2 | 10/2009 | Ressemann et al. |
| 7,697,996 B2 | 4/2010 | Manning et al. |
| 7,717,899 B2 | 5/2010 | Bowe et al. |
| 7,736,355 B2 | 6/2010 | Itou et al. |
| 7,762,984 B2 | 7/2010 | Kumoyama et al. |
| 7,763,012 B2 | 7/2010 | Petrick et al. |
| 7,959,603 B2 | 6/2011 | Wahr et al. |
| 8,048,032 B2 | 11/2011 | Root et al. |
| 8,142,413 B2 | 3/2012 | Root et al. |
| 8,292,850 B2 | 10/2012 | Root et al. |
| 8,814,890 B2 | 8/2014 | Miyata et al. |
| RE45,380 E | 2/2015 | Root et al. |
| 8,996,095 B2 | 3/2015 | Anderson et al. |
| 9,144,662 B2 | 9/2015 | Caprio et al. |
| RE45,760 E | 10/2015 | Root et al. |
| RE45,776 E | 10/2015 | Root et al. |
| 9,352,123 B2 | 5/2016 | Zhou et al. |
| RE46,116 E | 8/2016 | Root et al. |
| 9,486,611 B2 | 11/2016 | Petersen et al. |
| 10,173,029 B2 | 1/2019 | Webster et al. |
| RE47,379 E | 5/2019 | Root et al. |
| 10,751,514 B2 | 8/2020 | Brenizer et al. |
| 11,712,544 B2 | 8/2023 | Brenizer et al. |
| 2001/0016712 A1 | 8/2001 | Hamilton |
| 2002/0165598 A1 | 11/2002 | Wahr et al. |
| 2003/0195546 A1 | 10/2003 | Solar et al. |
| 2003/0233117 A1 | 12/2003 | Adams et al. |
| 2004/0010280 A1 | 1/2004 | Adams et al. |
| 2004/0087933 A1 | 5/2004 | Lee et al. |

(56) References Cited

U.S. PATENT DOCUMENTS

| | | | |
|---|---|---|---|
| 2004/0127927 A1 | 7/2004 | Adams | |
| 2004/0236215 A1 | 11/2004 | Mihara et al. | |
| 2005/0004523 A1 | 1/2005 | Osborne et al. | |
| 2005/0015073 A1 | 1/2005 | Kataishi et al. | |
| 2005/0182437 A1 | 8/2005 | Bonnette et al. | |
| 2006/0247661 A1 | 11/2006 | Richards et al. | |
| 2007/0260219 A1 | 11/2007 | Root et al. | |
| 2008/0082045 A1 | 4/2008 | Goldfarb et al. | |
| 2008/0243171 A1 | 10/2008 | Ressemann et al. | |
| 2009/0005755 A1 | 1/2009 | Keith et al. | |
| 2009/0264865 A1 | 10/2009 | Kawai | |
| 2013/0072904 A1 | 3/2013 | Musbach et al. | |
| 2013/0116701 A1 | 5/2013 | Wang et al. | |
| 2013/0197483 A1 | 8/2013 | Anderson et al. | |
| 2013/0289697 A1 | 10/2013 | Baker et al. | |
| 2014/0018773 A1* | 1/2014 | Wang | A61M 25/04 |
| | | | 604/528 |
| 2014/0025004 A1 | 1/2014 | Falk et al. | |
| 2014/0039461 A1 | 2/2014 | Anderson et al. | |
| 2014/0081243 A1 | 3/2014 | Zhou et al. | |
| 2014/0142506 A1 | 5/2014 | Prindle et al. | |
| 2014/0276618 A1 | 9/2014 | Caprio et al. | |
| 2015/0051633 A1 | 2/2015 | Sina | |
| 2015/0151090 A1 | 6/2015 | Sutton et al. | |
| 2015/0282821 A1 | 10/2015 | Look et al. | |
| 2016/0121080 A1 | 5/2016 | Cottone | |
| 2016/0346515 A1 | 12/2016 | Buller et al. | |
| 2017/0042571 A1* | 2/2017 | Levi | A61M 25/0113 |
| 2017/0296783 A1* | 10/2017 | Connolly | A61M 25/09 |
| 2017/0354800 A1* | 12/2017 | O'Donovan | A61M 25/0043 |
| 2018/0161547 A1 | 6/2018 | Brenizer et al. | |
| 2019/0247619 A1 | 8/2019 | Brenizer et al. | |
| 2020/0338317 A1 | 10/2020 | Brenizer et al. | |
| 2021/0008342 A1 | 1/2021 | Buller et al. | |
| 2021/0008343 A1 | 1/2021 | Brenizer et al. | |
| 2021/0008355 A1 | 1/2021 | Peterson et al. | |
| 2022/0313950 A1 | 10/2022 | Brenizer et al. | |

FOREIGN PATENT DOCUMENTS

| | | | |
|---|---|---|---|
| EP | 0313558 | B1 | 1/1991 |
| EP | 0380873 | B1 | 5/1994 |
| EP | 0365993 | B1 | 12/1994 |
| EP | 0881921 | A1 | 12/1998 |
| EP | 1084728 | A1 | 3/2001 |
| EP | 0992260 | B1 | 9/2007 |
| JP | 2004275435 | A | 10/2004 |
| WO | 1984003633 | A1 | 9/1984 |
| WO | 1997037713 | A1 | 10/1997 |
| WO | 2000024451 | A9 | 11/2000 |
| WO | 2016191415 | A1 | 12/2016 |
| WO | 2017019900 | A1 | 2/2017 |
| WO | 2020112293 | A1 | 6/2020 |

OTHER PUBLICATIONS

Bertrand, Michel E. "The Evolution of Cardiac Catheterization and Interventional Cardiology," European Society of Cardiology, 2006, 10 pages.

Bonzel, T. et al. "The Sliding Rail System (Monorail): Description of a New Technique for Intravascular Instrumentation and its Application to Coronary Angioplasty," Z. Kardiol. 76, Supp. 6 (1987), pp. 119-122.

European Extended Search Report mailed Jun. 22, 2022, in EP Application No. 22165689.5.

Iqbal et al. "Coronary stents: historical development, current status and future directions," British Medical Bulletin, 2013, 106: 193-211.

Vascular Solutions, Inc. "GuideLiner V3 catheter: Guide Extension Catheter with Half-Pipe Technology" [Brochure], Dec. 2013, Minneapolis, MN.

PCT International Preliminary Report on Patentability mailed Dec. 16, 2019, in PCT application No. PCT/US2019/016235.

PCT International Search Report mailed Apr. 29, 2019, in PCT application No. PCT/US2019/016235.

Takahashi et al. "New Method to Increase a Backup Support of a 6 French Guiding Coronary Catheter," Catheterization and Cardiovascular Interventions 63:452-456 (2004), 5 pages; Published online in Wiley InterScience (www.interscience.wiley.com).

Tully, Shawn. "Blood Feud This little piece of metal is worth $4.5 billion this year, generates more profits than a blockbuster drug, and has sparked one of the weirdest corporate battles ever. It could also save your life." CNN Money, May 31, 2004, 5 pages. Retrieved Jan. 14, 2019 on the Internet: https://money.cnn.com/magazines/fortune/fortune_archive/2004/05/31/370693/index.htm.

* cited by examiner

GUIDE EXTENSION CATHETER

CLAIM OF PRIORITY

This application is a divisional application of U.S. patent application Ser. No. 17/843,687, filed Jun. 17, 2022, now abandoned, which is a continuation application of U.S. patent application Ser. No. 16/264,803, filed Feb. 1, 2019, now abandoned, which claims the benefit of priority under 35 U.S.C. § 119(e) to U.S. Provisional Patent Application Ser. No. 62/630,321, entitled "GUIDE EXTENSION CATHETER" and filed on Feb. 14, 2018, wherein each of these applications are herein incorporated by reference in their entirety.

TECHNICAL FIELD

This patent document relates to medical devices. More particularly, but not by way of limitation, this patent document relates to guide extension catheters for use with guide catheters.

BACKGROUND

A guide catheter can be employed to gain access to a blood vessel and deliver interventional devices, such as guidewires, balloon catheters, stents or stent catheters, beyond the guide catheter's distal end. Poor alignment between the guide catheter and the ostia of the blood vessel can make it difficult to deliver interventional devices to a target location within or distal to the vessel. To improve coaxial alignment between the guide catheter and the blood vessel, a narrower guide extension catheter may be used. A growing desire to use larger guide catheters in tandem with smaller guide extension catheters increases the likelihood of stent-device interaction at the transition of the guide extension catheter.

OVERVIEW

The present inventors recognize that there is a need to provide guide extension catheters that are compatible with larger guide catheters for performing interventional procedures in challenging anatomy, e.g., narrow blood vessels, often harboring robust occlusions. A guide extension catheter that includes tapered guide extension tubing can be used in conjunction with a guide catheter to access discrete regions of coronary or peripheral vasculature and to facilitate accurate placement of interventional devices without causing collar transition interactions. The guide extension catheter can also include a slidable manipulation member and/or in some examples, a concave track leading into the guide extension tubing.

Guide extension catheters and related methods are disclosed in this patent document. A guide extension catheter can comprise an elongate tube member (also referred to as guide extension tubing) and a push member. At least a portion of the guide extension tubing can be tapered, enabling interventional devices to be funneled to distal portions of the extension tubing, which can be sized smaller to fit into distal vessels.

These and other embodiments and features of the present guide extension catheters and related methods will be set forth, at least in part, in the following Detailed Description. This Overview is intended to provide non-limiting embodiments of the present subject matter—it is not intended to provide an exclusive or exhaustive explanation of the disclosed embodiments. The Detailed Description below is included to provide further information about the present guide extension catheters and methods.

BRIEF DESCRIPTION OF THE DRAWINGS

In the drawings, like numerals can be used to describe similar features and components throughout the several views. The drawings illustrate generally, by way of example, but not by way of limitation, various embodiments discussed in this patent document.

The drawings are not necessarily to scale. Certain features and components may be shown exaggerated in scale or in schematic form, and some details may not be shown in the interest of clarity and conciseness.

DETAILED DESCRIPTION

This patent document discloses guide extension catheters to be placed within guide catheters for providing support and guidance in a vessel when percutaneously advancing interventional devices, such as guidewires, balloon catheters, stents or stent catheters. A guide extension catheter is configured to be passed through a main lumen of a guide catheter so that its distal end portion can be extended past a distal end of the guide catheter and into the desired vessel while its intermediate portions remain within the guide catheter. The guide extension catheter improves the ability of the guide catheter to remain seated in the desired vessel's ostium or branch during an interventional procedure.

It is believed that the present guide extension catheters will find great utility by interventional cardiologists performing percutaneous transluminal coronary interventions. Although the remainder of this patent document generally discusses and illustrates such uses, it should be understood that the guide extension catheters can also be used for treating other non-coronary diseased vessels or other hollow structures (e.g., biliary tract, ureter, etc.) throughout a patient's body where interventional devices are or can be employed.

Figure 1:
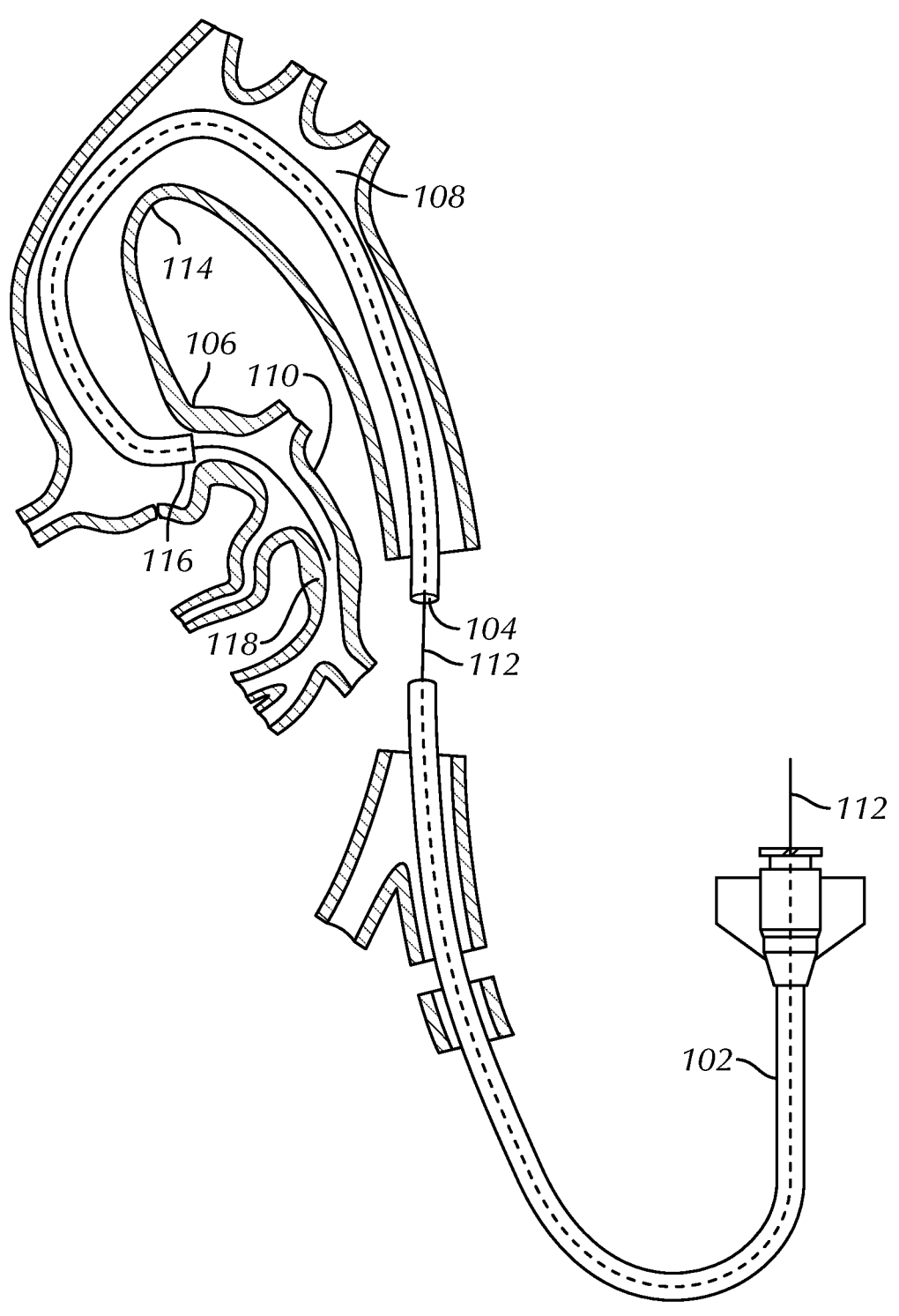
FIG. 1 illustrates a plan view of a guide catheter advanced through an aorta to an ostium of a coronary vessel.

Minimally-invasive cardiac interventions are utilized throughout the world and include the use of a guidewire 112 and a guide catheter 102, as illustrated in FIG. 1. The guidewire 112 is an elongate, small-diameter member designed to navigate vessels to reach a diseased site or vessel segment of interest. Guidewires come in two basic configurations: solid steel or nitinol core wires and solid core wire wrapped in a smaller wire coil or braid. The guide catheter 102 is an elongate tube member defining a main lumen 104 along its length. The guide catheter 102 can be formed of polyurethane, for example, and can be shaped to facilitate its advancement to a coronary ostium 106 (or other region of interest within a patient's body). In the embodiment of FIG. 1, a 6 F, 7 F or 8 F guide catheter 102, where F is an abbreviation for the French catheter scale (a unit to measure catheter diameter (1 F=⅓ mm)), can be inserted at a femoral or radial artery and advanced through an aorta 108 to a position adjacent to the ostium 106 of a coronary artery 110.

In a typical procedure, the guidewire 112 and guide catheter 102 are advanced through the arch 114 of the aorta 108 to the ostium 106. The guidewire 112 or, alternatively, a more flexible treatment guidewire replacing guidewire 112 is then advanced beyond the ostium 106 and into the coronary artery 110. The diameter and rigidity of the guide catheter's distal end 116 oftentimes does not permit the guidewire or a later-inserted interventional device to be advanced beyond the ostium 106 and into the coronary artery 110.

Maintaining the position of the guide catheter's distal end 116 at the ostium 106 can facilitate the guidewire 112 or other interventional device successfully reaching the diseased site (e.g., a stenotic lesion 118) through its further distal advancement. With the guide catheter 102 in position, force can be applied to the guidewire's proximal end to push the guidewire 112 to and beyond the lesion 118, and a treating catheter (optionally including a balloon or stent) can be passed over the guidewire 112 to treat the site. The application of force to the guidewire 112 or the treating catheter can sometimes cause the guide catheter 102 to dislodge from the ostium 106 of the coronary artery 110, and, in such instances, the guidewire or treating catheter must be further distally advanced independently of the guide catheter's alignment and support to reach the lesion 118. This can occur in the case of a tough stenotic lesion 118 or tortuous anatomy, where it is difficult to pass the guidewire 112 or the treating catheter to and beyond the lesion. A heart's intrinsic beat can also cause the guide catheter's distal end 116 to lose its positioning or otherwise be shifted so that it no longer is positioned to align and support the guidewire 112 or the treating catheter into the portion of the coronary artery 110 including the lesion 118.

Figure 2:
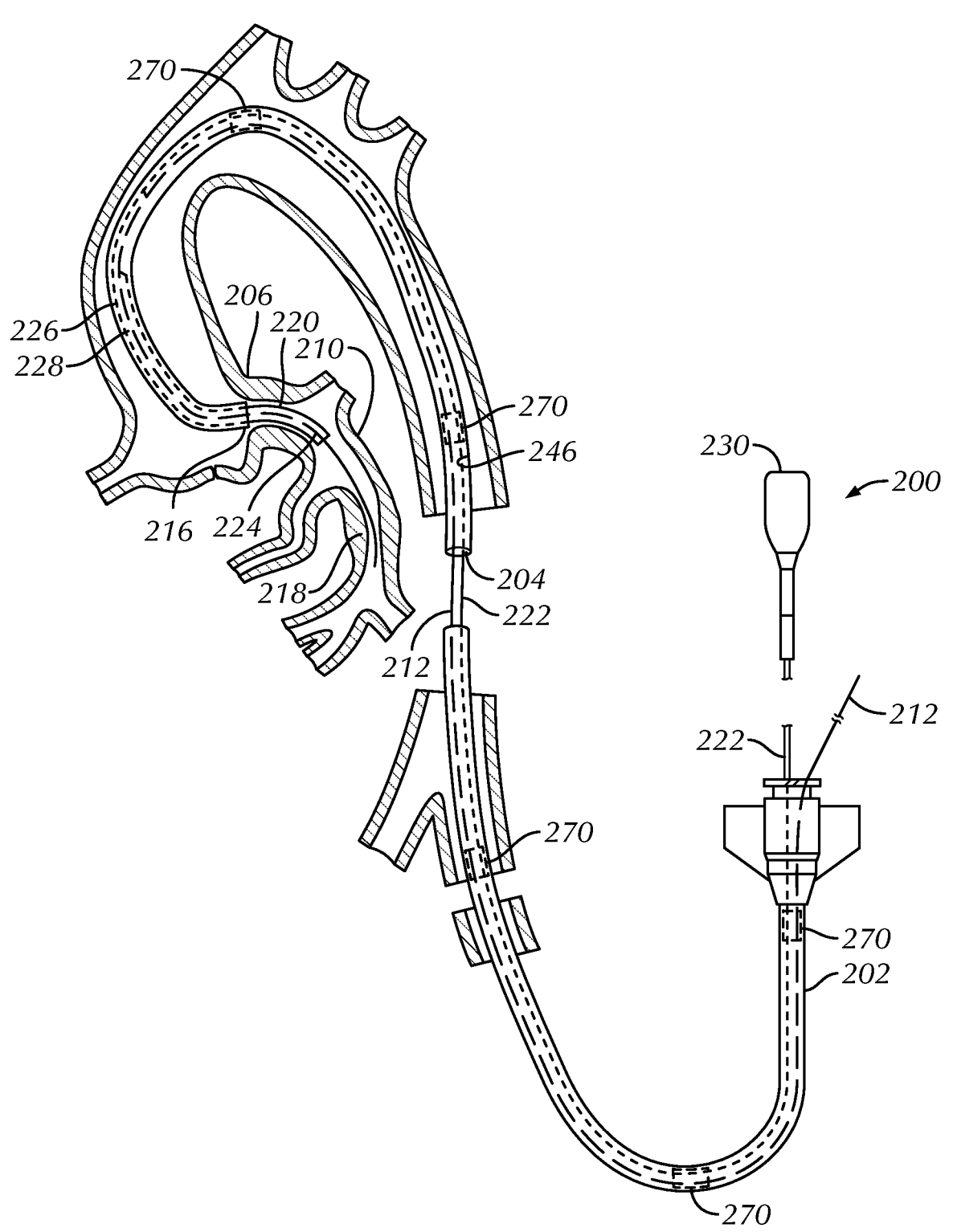
FIG. 2 illustrates a plan view of a guide extension catheter, as constructed in accordance with at least one embodiment, used in conjunction with a guide catheter for the delivery of an interventional device into an occluded vessel for treatment.

As illustrated in FIG. 2, the present guide extension catheter 200 can improve access to a coronary artery 210 and a stenotic lesion 218. The guide extension catheter 200 can include a relatively flexible elongate tube member 220 and a push member 222 having a collective length that is greater than a length of a guide catheter 202 (e.g., 130 cm-175 cm). An outer diameter of the tube member 220 can be sized to permit insertion of its distal end portion 224 into a coronary artery or its branches containing the lesion 218, thereby providing alignment and support for an interventional device (e.g., a treating catheter) beyond the distal end 216 of the guide catheter 202 to the lesion and beyond. The extension of the tube member 220 into the smaller-sized artery or branch also serves to maintain the position of the guide catheter 202 at an artery's ostium 206 during a procedure.

The operating physician can advance the narrow, distal end portion 224 of the tube member 220 over a guidewire 212 and through and beyond the guide catheter's distal end 216 into the coronary artery 210. A wider, proximal end portion 226 of the tube member 220 can remain within the guide catheter 202. The physician can then deliver the treating catheter over the guidewire 212, through a main lumen 204 of the guide catheter 202, and through a lumen 228 of the tube member 220 until the working portion of the treating catheter is located beyond the distal end portion 224 of the tube member. The operating physician can then treat the lesion 218 using standard techniques.

In general, the lumen 228, and hence the tube member 220, can be sized and shaped to pass one or more interventional devices such as the guidewire and the treating catheter therethrough. The cross-sectional shape of the lumen 228 can vary along the length of the tube member 220. For instance, the proximal portion 226 of the tube member can have a larger diameter than the distal portion 224. The proximal and distal portions can be separated by a tapered portion 225. The length of each cross-sectionally-sized portion of the tube member 220 can also vary, and in some examples, the distal portion 224 of the tube member is the longest. The largest outer diameter of the tube member 220 can assume maximum cross-sectional dimensions that allow the tube member 220 to coaxially slide into and through the guide catheter 202. In other embodiments, the outer cross-sectional dimensions of the tube member 220 can be less than the allowable maximum. For example, in an 8 F guide catheter, the tube member 220 can have a 7 F, 6 F, 5 F, 4 F or lesser diameter, depending on the location along the tube member. In some embodiments, the largest diameter of the lumen 228 of the tube member 220 is not more than about one French size (e.g., 0.013-0.015 inches) smaller than a diameter of the lumen 204 of the guide catheter 202. In some examples, the difference in diameter between the proximal portion 226 and distal portion 224 of the tube member may be about 1 F, 2 F, 3 F, or 4 F. The length of the tube member 220 can be substantially less than the length of the guide catheter 202; however, the tube member 220 can be designed with any length according to a desired application, such as about 6 cm-45 cm.

The push member 222 can be operably attached to the proximal end portion 226 of the tube member 220 and can extend proximally from this attachment to a handle (also referred to as a manipulation) member 230 accessible to an operating physician outside of a patient's body. The handle member 230 and the push member 222 can allow the physician to position the tube member 220 between a first position, entirely within the guide catheter 202, and the illustrated second position, in which the tube member's distal end 224 extends beyond that of the guide catheter 202 and into the coronary artery 210. The push member 222 can include one or more tubular bands 270 or other means along its length to urge the push member to one side of the guide catheter's inner wall surface 246.

Figure 3:
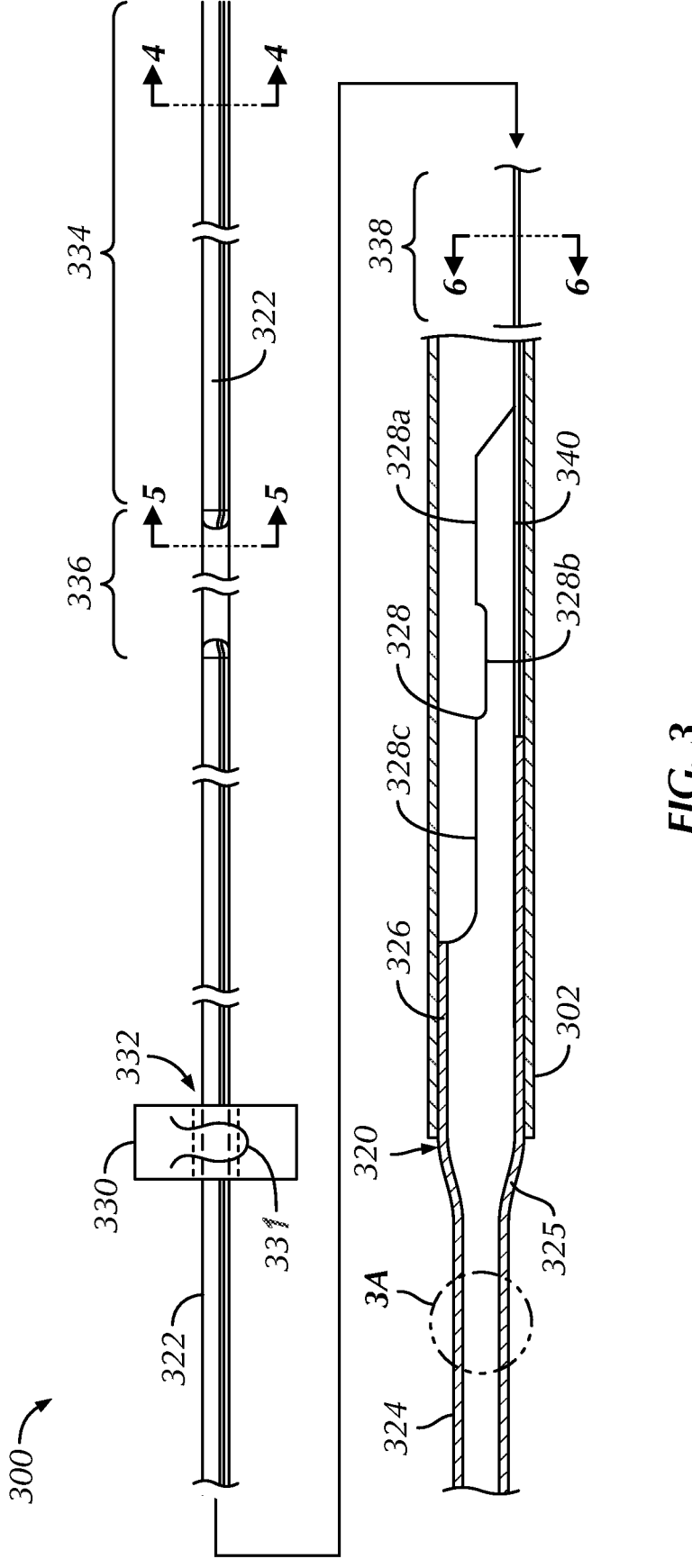
FIG. 3 illustrates a side view of a guide extension catheter, as constructed in accordance with at least one embodiment, partially within a sectioned guide catheter.

FIG. 3 illustrates a side view of a guide extension catheter 300 partially positioned within a guide catheter 302. This side view illustrates in greater detail the components of the extension catheter 300, including a relatively flexible elongate tube member 320 and a push member 322, as well as the distinct portions of the tube member defined by different diameters. For instance, the tube member 320 in the example shown defines a narrow distal portion 324, a tapered middle portion 325, and a wider proximal portion 326. The proximal portion 326 is connected to a concave track 328 which defines variable degrees of enclosure along its length. As further shown, the push member 322 can be coupled with a manipulation member 330 configured to facilitate pushing of the extension catheter 300 into the guide catheter 302.

The diameter variation of the tube member 320 uniquely equips the guide extension catheter 300 for complex percutaneous coronary interventional cases performed in distal, narrow blood vessels. Such cases may require a relatively large guide catheter, e.g., 7 F or 8 F, in combination with a smaller guide extension profile, e.g., 5 F or 6 F. Embodiments of the tube member 320 can include a proximal end portion 326 having a diameter of about 7 F or 8 F, which narrows along tapered portion 325 to a diameter of about 6 F in the distal end portion 324. The length of each portion of tube member 320 can vary. In one embodiment, the proximal end portion 326 may be about 5 cm long, the tapered portion 325 may be about 5 mm long, and the distal end portion 324 may be about 20 cm long. In other examples, the length of the proximal portion 326 may range from about 1 cm to about 10 cm, the length of the distal portion 324 may range from about 10 cm to about 30 cm, and the length of the tapered portion 325 may range from about 2 mm to about 20 mm. Generally, the narrow distal end portion 324 constitutes the majority of the length of the tube member 320, and in some examples, may be at least twice as long as the tapered portion 325 and the proximal portion 326 combined. The length of the tapered portion 325 may be modified without adjusting the difference in diameter between the proximal and distal end portions of the tube member 320, such that the pitch of the tapered surfaces is steeper for shorter tapered portions and more gradual for longer tapered portions.

Figure 3A:
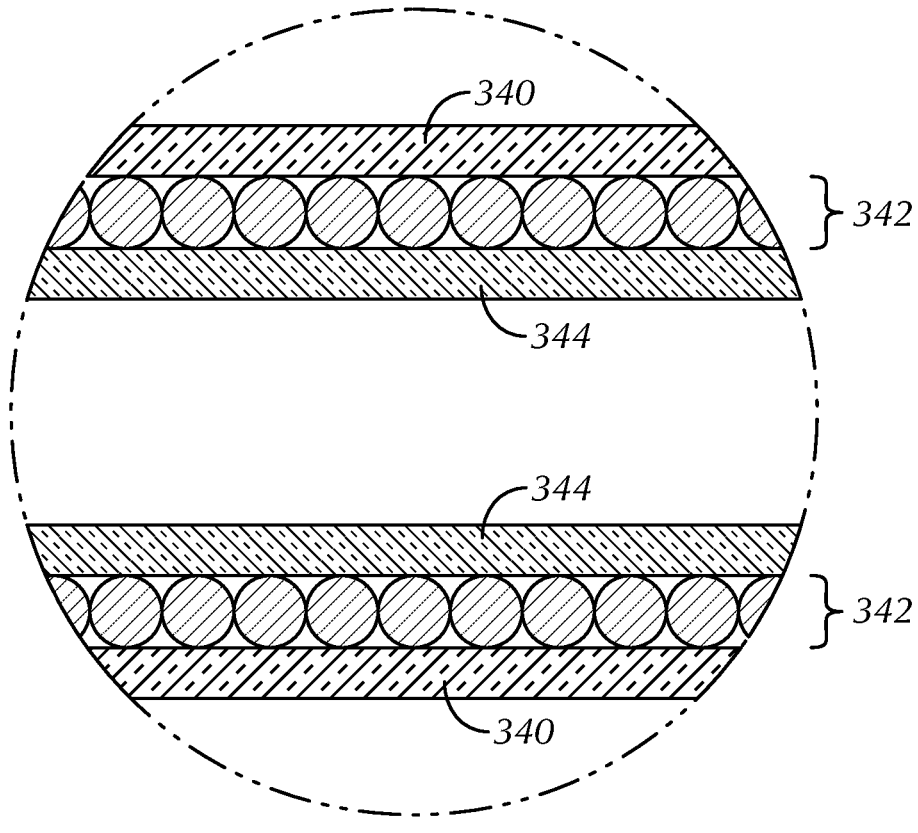
FIG. 3A illustrates an enlarged detail side view of a portion of the guide extension catheter of FIG. 3 that is enclosed in the dashed circle indicated by reference character "3A".

The tube member 320 can be formed from an inner polymer layer, an outer polymer layer, and a reinforcement member (e.g., braid or coil) disposed between the polymer layers. FIG. 3A illustrates an enlarged detail side view of a portion of the tube member 320 including a reinforcement member 342 disposed between an outer polymer layer 340 and an inner polymer layer 344. Referring again to FIG. 3 and FIG. 3A, the inner polymer layer can be composed of, or coated with, silicone, polytetrafluoroethylene (PTFE) or another lubricious material to provide a slippery surface for received interventional devices. The outer polymer layer can include one or more flexible materials, such as polyurethane, polyethylene or polyolefin of sequentially diminishing durometers along the tube member's length, and it can be coated with a friction-reducing material (e.g., a hydrophilic material) to facilitate insertion and trackability through vasculature and a guide catheter. The reinforcing braid or coil can be formed of stainless steel, nitinol or a platinum alloy, for example, and can extend between the polymer layers along at least a portion of the tube member's length.

Methods of manufacturing the guide extension catheters described herein may involve stretching an inner PTFE lining of the tapered, elongate tube member 320. Because the PTFE lining may require excess stretching relative to manufacturing of comparable, but non-tapered tube members, the outer surface of the lining can be etched to maintain the desired polymer chemistry of the PTFE, thereby ensuring adhesion between the fluoropolymers of the lining and an outer polymer layer (e.g., Pebax®) wrapping.

The reinforcement member disposed between the polymer layers of the elongate tube member 320 can be configured and assembled in multiple ways. For example, if the reinforcement member disposed between the polymer layers of the elongate member 320 is a coil, three general types of coils may be used, each coil coupled with other components of the tube member 320 in a distinct manner. If the size of the coil matches the smaller distal portion 324 of the tube member 320, the coil can be first loaded over the distal portion 324 and then turned up against the pitch of the tapered portion 325. By turning the coil against the pitch of the tapered portion 325, the coil diameter will be enlarged such that the coil can be loaded over the taper and the larger diameter of the proximal portion 326. If the size of the coil is larger, such that it approximately matches the larger diameter of the proximal portion 326, the coil can be first loaded onto the proximal portion 326 and then turned down to match the smaller diameter of the tapered 325 portion and distal portion 324. If the size of the coil is between the smaller diameter of the distal portion 324 and the larger diameter of the proximal portion 326, coupling the coil to the tube member 320 may involve a hybrid approach of winding the coil up and down the pitch of the tapered portion 325.

In certain embodiments, the push member 322 can include a plurality of segments or portions having different stiffness and flexibility profiles to provide the guide extension catheter 300 with a desired combination of pushing force and vessel placement capabilities. In some examples, the push member 322 can include three segments 334, 336, 338 having different stiffness and flexibility profiles: relative high stiffness and low flexibility at a proximal end portion of the push member, relative medium stiffness and flexibility at a proximal end portion of the push member, and relative low stiffness and high flexibility at a distal portion of the push member. In some embodiments, the length of the first segment 334 makes up between 50% to 90% of the entire length of the guide extension catheter 300, the length of the third segment 338 makes up between 2% to 10% of the catheter's length, and the remaining length can be attributed to the second segment 336. More or less segments of differing stiffness and flexibility profiles can also be used and accomplished through variation of one or more of materials, geometrical shapes or geometrical sizes of the push member 322. The push member 322 can be an elongated solid wire of constant or varying dimensions and can made of a polymeric or metallic material, such as high tensile stainless steel (e.g., 304V, 304L or 316LV), mild steel, nickel-titanium alloys, nickel-chromium-molybdenum alloys, nickel-copper alloys, nickel-tungsten alloys or tungsten alloys. The push member 322 can be coated with a hydrophilic, silicone or other friction-reducing material. A handle member (FIG. 2) at the push member's proximal end can be formed of a polycarbonate material, for example.

The manipulation member 330 facilitates pushing of the extension catheter 300 through the guide catheter 302. As shown, the manipulation member 330 can comprise a tab 331 and defines a hole 332, which may be cylindrical, through which the push member 322 extends such that the manipulation member 330 is configured to be that is slidable along the push member 322. In operation, the manipulation member 330 can be initially positioned proximal to the elongate tube member 320, and then slid proximally along the push member 322 as the extension catheter 300 is urged distally, toward the treatment site. In some examples, the manipulation member 330 is engageable with the push member 322 via a compressive force applied to the tab 331 by a user, e.g., a manual force applied by a user's thumb.

The concave track 328 can be eccentrically coupled to a distal end portion 340 of the push member 322 at its periphery or circumference and can provide a smooth transition between the tube member 320 and the push member 322. The concave track 328 can be bonded between or integrated with the proximal end portion 326 of the tube member 320 and/or the distal end portion 340 of the push member 322. Metallic or polymeric structures forming the concave track 328 can become less stiff and more flexible in a proximal-to-distal direction to provide a gradual flexibility transition between the more rigid push member 322 and the more flexible tube member 320.

The degree of enclosure defined by the concave track 328 can vary along the length of the track. In an embodiment, a first segment 328a of the concave track 328 can define an approximately 200° enclosure, a second segment 328b of the concave track can define an approximately 170° enclosure, and a third segment 328c, closer to the tube member 320, can define an approximately 200° enclosure, which transitions to 360° just before reaching the most proximal end of the tube member's proximal portion 326. Accordingly, the concave track 328 may transition, proximally to distally, from more enclosed to less enclosed, and back to more enclosed before reaching the proximal end portion 326 of the tube member 320. The specific degree of enclosure defined by each portion of the concave track 328 may vary. For example, the degree of enclosure defined by each portion may be increased or decreased by up to 5°, 10°, 15°, 20°, 25°, 30°, 40°, 50°, 60°, or more. The intermediary valley of the concave track, i.e., the second segment 328b, along with the embedded push member 322, may be urged to one side of the guide catheter's inner wall surface such that the track 328 and push member 322 may be concentrically aligned within guide catheter 302, thereby providing a clear path through the guide catheter and into the tube member 320 for a guidewire and a treating catheter. This clear path can eliminate twisting and prevent a guidewire, e.g., guidewire 212, from becoming entangled with, e.g., wrapped around, the push member 322 during use of the guide extension catheter 300. Alleviation of twisting may be especially apparent in operations requiring multiple, simultaneously inserted guidewires.

In some embodiments, the concave track 328 can define a partially cylindrical opening, e.g., resembling a half-pipe, and having a length of about 1 cm to about 18 cm, 20 cm, 22 cm, 24 cm, 26 cm, or more. In one example, the concave track 328 may be about 17 cm long. In various embodiments, the length of each discernible portion 328a, 328b, 328c of the concave track 328 may range from about 1 cm, 2 cm, 4 cm, 6 cm, 8 cm, 10 cm, or 12 cm. The length of each portion 328a, 328b, 328c may be the same or different. The concave track 328 is accessible from a longitudinal side defined transverse to a longitudinal axis of the tube member 320 and provides a larger area to receive an interventional device into the tube member than an area associated with an opening oriented perpendicular to the longitudinal axis of the tube member 320. Optionally, the concave track 328 can be sized larger than the proximal end portion 326 of the tube member 320 to more effectively align and funnel a treating catheter across the coupling transition and into the tube member 320. This larger size of the concave track 328 can be accomplished by incorporating a nickel-titanium alloy, for example, which can expand post-implant to a size of the guide catheter's inner wall surface.

Markers on the push member 322 and/or the tube member 320 can allow an operating physician to identify positioning of the guide extension catheter's components relative to patient anatomy, the guide catheter 302, and any international devices used during a procedure. For example, one or more depth markers can be printed on an outer surface of the push member 322 and can be positioned at predetermined lengths relative to a distal end of the tube member 320. One or more radiopaque marker bands can be positioned on the tube member 320. The marker bands can be composed of tungsten, platinum or an alloy thereof and can have a metallic band structure. Alternatively, for space conservation reasons, the marker bands can be formed by impregnating portions of the tube member 320 with a radiopaque filler material, such as such as barium sulfate, bismuth trioxide, bismuth carbonate, powdered tungsten, powdered tantalum or the like. A first marker band can be positioned slightly distal to a fully-round entrance of the tube member 320 and a second marker band can be positioned near the tube member's distal end, for example.

Figure 4:
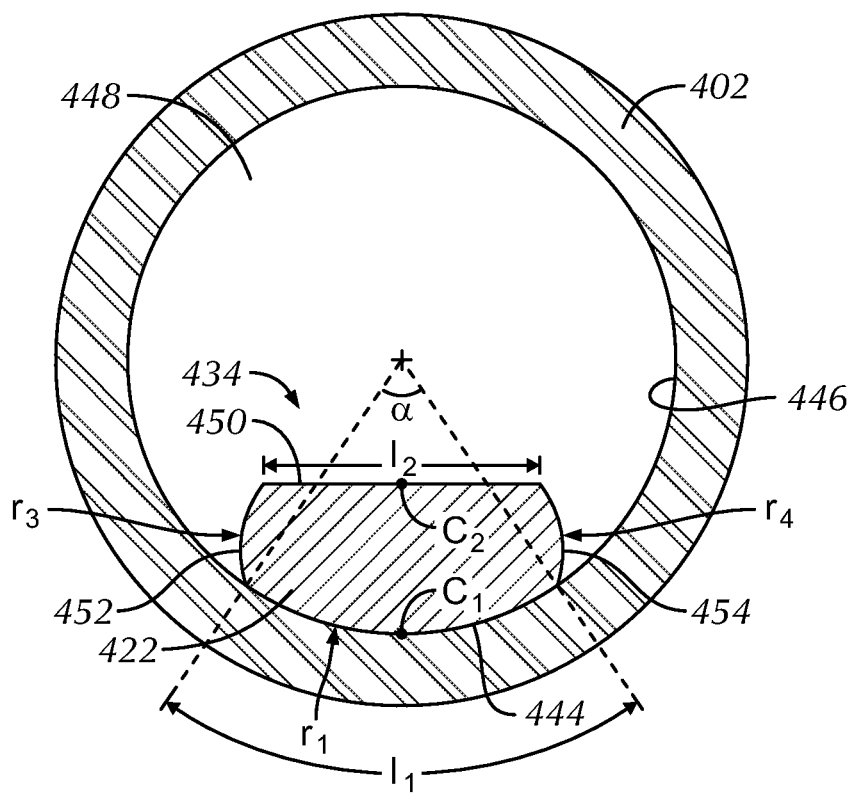
FIGS. 4-6 illustrate cross-sectional views along the length of a guide extension catheter, as constructed in accordance with at least one embodiment, within a guide catheter.

FIG. 4 illustrates a cross-sectional view of a proximal end portion 434 of a push member 422, such as along line 4-4 of FIG. 3, within a guide catheter 402. The cross-section can be defined by an arcuate first surface 444 configured to engage an inner wall surface 446 of the guide catheter 402 along an arc length ($l_1$) (e.g., 0.030 in) defined by a guide catheter central angle ($\alpha$) of at least 20 degrees, at least 30 degrees, at least 40 degrees, at least 50 degrees or at least 60 degrees, with greater arc lengths ($l_1$) associated with greater central angles ($\alpha$). The arcuate or curved shape of the first surface 444 follows the inner wall surface 446 of the guide catheter 402 providing smooth relative movements between the guide extension catheter and the guide catheter. The arcuate shape of the first surface 444 can also help to maximize axial or column strength of the push member 422 for force transfer from an operating physician to the rest of the guide extension catheter without reducing the effective delivery area 448 within the guide catheter 402 through which an interventional device can be advanced. In an embodiment, the first surface 444 can have the same or substantially the same radius of curvature ($r_1$) as the guide catheter's inner wall surface 446, such as a radius of curvature of about 0.035 in.

A second surface 450 of the proximal end portion's cross-section, which is positioned opposite the first surface 444, can be flat or substantially flat and have a length ($l_2$) (e.g., 0.026 in) that is less than the arc length ($l_1$) of the first surface. The second surface 450 can be spaced furthest from the first surface at its center point ($c_2$). In an embodiment, the center point ($c_2$) of the second surface 450 is at least 0.010 in (e.g., 0.014 in) from a center portion (c1) of the first surface 444. In an embodiment, a distance between center points ($c_1$, $c_2$) of the first and second surfaces 444, 450 can be between 40-60% of the arc length ($l_1$) of the first surface.

The cross-section at the proximal end portion of the push member 422 can be further defined by third and four arcuate surfaces 452, 454 that connect the first and second surfaces 444, 450. The third and four surfaces 452, 454 can have a radius of curvature ($r_{3,4}$) less than the radius of curvature ($r_1$) of the first surface 444. In an embodiment, the radius of curvature ($r_1$) of the first surface (e.g., 0.035 in) is at least three times greater than the radius of curvature ($r_{3,4}$) of the third and fourth surfaces (e.g., 0.010 in).

It has been found that this cross-sectional configuration of the proximal end portion 434 of the push member 422 can be desirable for a number of reasons. The configuration, which resembles a bread loaf in its cross-sectional shape, can increase the push force capability and the torque control of the push member 422 as compared to a flat rectangular ribbon. Accordingly, greater axial and rotational force applied by the operating physician to the push member's proximal end portion 434 can be transmitted to the tube member. In this manner, the tube member can more reliably be urged through obstructions or into a tortuous portion of the patient's vasculature.

Figure 5:
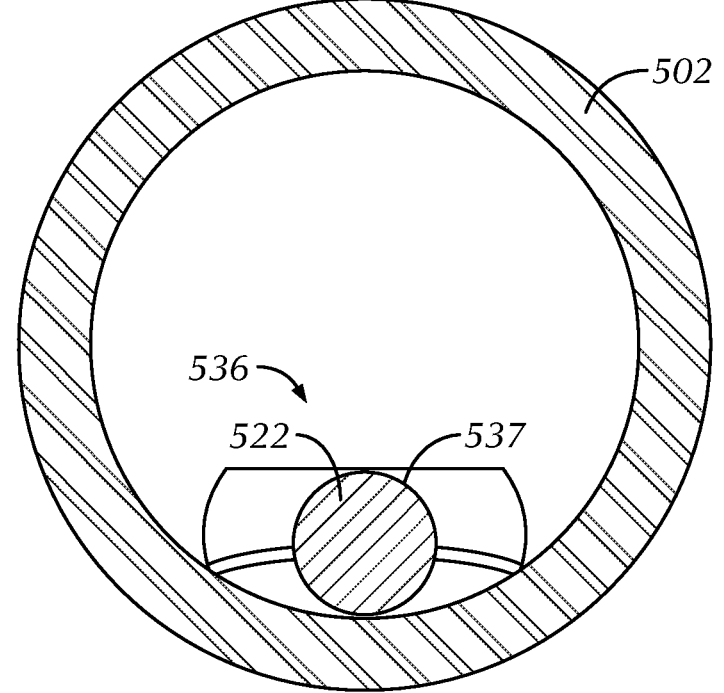

FIG. 5 illustrates a cross-sectional view of an intermediate portion 536 of a push member 522, such as along line 5-5 of FIG. 3, within a guide catheter 502. As shown, the intermediate portion 536 can be circular or oval in cross-section and defined by a circumferential surface 537, which can reduce the tendency for a guidewire to become engaged with the push member 522 during use. In an embodiment, the circumferential surface 537 has a diameter of about 0.013 in.

Alternatively, the intermediate portion 536 can be rectangular in cross-section and defined by first, second, third and fourth flat surfaces, or can be bread loaf in cross-section and defined by three arcuate surfaces and one flat surface like the proximal end portion. In these alternative embodiments, a distance change between center points of the first and second surfaces at the push member's proximal end portion (FIG. 4) to center points of the first and second surfaces at the push member's intermediate portion is less than a distance change between center points of the third and fourth surfaces at the push member's proximal end portion to center points of the third and fourth surfaces at the push member's intermediate portion.

Yet another alternative, the intermediate portion 536 can have a cross-section defined by arcuate first and second surfaces. An arcuate first surface can have the same or substantially the same radius of curvature as the guide catheter's inner wall surface. An arcuate second surface can extend from a first end of the first surface to a second end of the first surface. Regardless of shape, the cross-section of the intermediate portion 536 of the push member can define an area less than an area of the cross-section of the proximal end portion (FIG. 4) of the push member 522.

Figure 6:
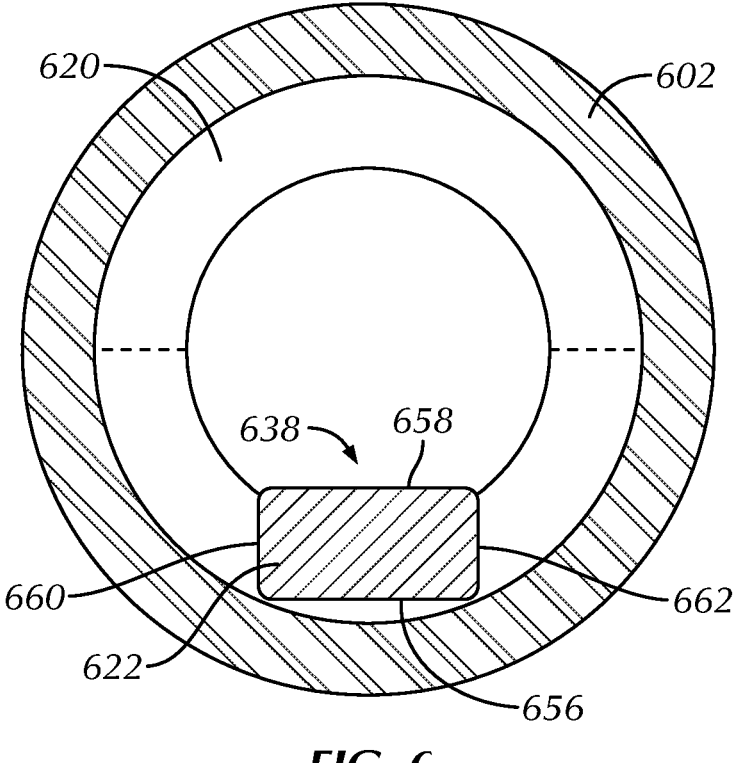

FIG. 6 illustrates a cross-sectional view of a distal end portion 638 of a push member 622, such as along line 6-6 of FIG. 3, within a guide catheter 602. The distal end portion 638 can be rectangular in cross-section and defined by first, second, third and fourth flat surfaces 656, 658, 660, 662. The cross-section of the distal end portion 638 can define an area less than an area of the cross-section of the proximal end (FIG. 4) and intermediate (FIG. 5) portions of the push member 622. In an embodiment, the first and second surfaces 656, 658 have a length of 0.020 in., and the third and fourth surfaces 660, 662 have a length of 0.010 in. The cross-section of the stiffer proximal end portion can gradually transition along the length of the push member 622 to the more flexible cross-section of the distal end portion 638, which can couple to a tube member 620. The flattened rectangular cross-section of the distal end portion 638 can provide sufficient attachment surface area to attach the push member 622 to the tube member 620. Alternatively, the distal end portion 638 can be bread loaf in cross-section and defined by three arcuate surfaces and one flat or substantially flat surface like the proximal end portion.

FIGS. 4-6 illustrate that the push member 422, 522, 622 of a guide extension catheter can be designed to be sufficiently small taking up relatively little space within the lumen of a guide catheter, while still being sufficiently sized and configured for exceptional pushability and kink resistance when advancing the extension catheter during an interventional procedure. Accordingly, use of the present guide extension catheters allows for an interventional device to be advanced through and beyond the guide catheter to reach a desired distal target location for intervention.

Figure 7:
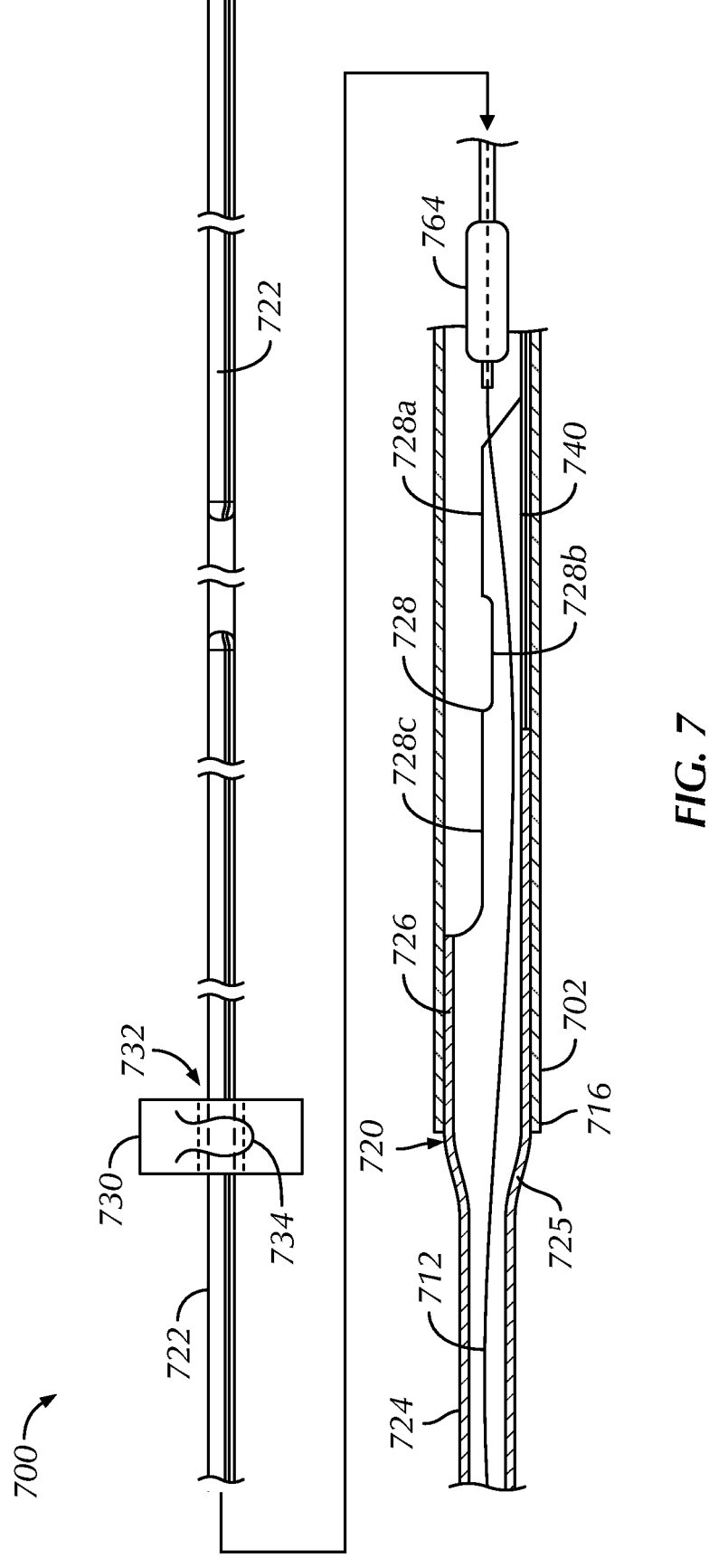
FIG. 7 illustrates a side view of a guide extension catheter, as constructed in accordance with at least one embodiment, and an interventional device partially within a sectioned guide catheter.

FIG. 7 illustrates a side view of a guide extension catheter 700 positioned within a guide catheter 702 and used in conjunction with a guidewire 712 and a treating catheter 764. As shown in FIG. 7, the guide extension catheter 700 can include a manipulation member 730 comprising a tab 734 and defining a hole 732 through which the push member 722 extends, such that the manipulation member 730 is configured to be slidable along the push member 722 and to be controllably engageable with the push member 722 via a compressive force applied to the tab 734 in a manner the same as or similar to that described above with respect to FIG. 3. Referring again to FIG. 7, with the guidewire 712 and the guide catheter 702 positioned as desired, a tube member 720 of the guide extension catheter 700 can be backloaded from its narrow distal end portion 724 onto a proximal end of the guidewire 712 and advanced through a hemostasis valve coupled to the guide catheter 702. As shown, the tube member 720 of the guide extension catheter 700 can be advanced beyond a distal end 716 of the guide catheter 702 under fluoroscopy. When so arranged, portions of the tube member 720 can engage an ostium and extend within a portion of a coronary artery to help maintain the position of the guide catheter 702 as the treating catheter 764 is advanced. The variable degree of enclosure provided by the concave track 728 at portions 728 *a*, 728 *b*, and 728 *c* may prevent twisting of the guidewire 712.

EXAMPLES

The above Detailed Description is intended to be illustrative and not restrictive. The above-described embodiments (or one or more features or components thereof) can be used in varying combinations with each other unless clearly stated to the contrary. Other embodiments can be used, such as by one of ordinary skill in the art upon reviewing the above Detailed Description. Also, various features or components have been grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment.

In Example 1, a guide extension catheter for use with a guide catheter can comprise an elongate tube member defining a lumen and three portions. Each portion can have a distinct diameter. The tube member can comprise a distal portion having a first diameter, a proximal portion defined by a second diameter which is larger than the first diameter but smaller than a lumen of the guide catheter, and a tapered portion, positioned between the distal portion and the proximal portion, defined by a variable diameter. The guide extension catheter can also include a push member eccentrically coupled relative to the tube member and extending proximally therefrom for slidably positioning the tube member within and partially beyond a distal end of the guide catheter. In addition, the guide extension catheter can include a concave track coupled to the tube member and the push member. The concave track can define a partially cylindrical opening leading into the tube member.

In Example 2, the guide extension catheter of Example 1 can optionally be configured such that the first diameter is about 6 F or less.

In Example 3, the guide extension catheter of Example 1 or 2 can optionally be configured such that the second diameter is about 7 F or greater.

In Example 4, the guide extension catheter of any one or any combination of Examples 1-3 can optionally be configured such that the distal portion is at least twice as long as the proximal portion and the tapered portion combined.

In Example 5, the guide extension catheter of any one or any combination of Examples 1-4 can optionally be configured such that the distal portion is about 20 cm long.

In Example 6, the guide extension catheter of any one or any combination of Examples 1-5 can optionally be configured such that the proximal portion is about 5 cm long.

In Example 7, the guide extension catheter of any one or any combination of Examples 1-6 can optionally be configured such that the tapered portion is about 5 mm long.

In Example 8, the guide extension catheter of any one or any combination of Examples 1-7 can optionally be configured such that the concave track defines an intermediary track portion that is less enclosed than a distal track portion and a proximal track portion.

In Example 9, the guide extension catheter of Example 8 can optionally be configured such that an enclosure of the intermediary portion is about 170°, an enclosure of the distal track portion is about 200°, and an enclosure of the proximal track portion is about 200°.

In Example 10, the guide extension catheter of any one or any combination of Examples 1-9 can optionally comprise a slidable manipulation member coupled with the push member. The slidable manipulation member can comprise a tab that defines a hole through which the push member is urged during insertion of the guide extension catheter through the guide catheter.

In Example 11, the guide extension catheter of any one or any combination of Examples 1-10 can optionally be configured such that a reinforcement member comprising a coil is coupled with the elongate tube member.

In Example 12, the guide extension catheter of Example 11 can optionally be configured such that the coil, in a relaxed state, defines a diameter that approximately matches the second diameter.

In Example 13, the guide extension catheter of Example 12 can optionally be configured such that the coil is wound down over the tapered portion during assembly.

In Example 14, the guide extension catheter of Example 11 can optionally be configured such that the coil, in a relaxed state, defines a diameter that approximately matches the first diameter.

In Example 15, the guide extension catheter of Example 14 can optionally be configured such that the coil is wound up over the tapered portion during assembly.

In Example 16, the guide extension catheter of Example 11 can optionally be configured such that the coil, in a relaxed state, defines a diameter that is between the first diameter and the second diameter.

In Example 17, the guide extension catheter of Example 16 can optionally be configured such that the coil is wound up over the proximal portion and wound down over the distal portion during assembly.

In Example 18, the guide extension catheter of any one or any combination of Examples 1-17 can optionally be configured such that the elongate tube member comprises an inner polymer layer.

In Example 19, the guide extension catheter of Example 18 can optionally be configured such that the inner polymer layer is stretched during assembly of the elongate tube member.

In Example 20, the guide extension catheter of Example 19 can optionally be configured such that after stretching, an outer surface of the inner polymer layer is etched.

Closing Notes:

The above Detailed Description includes references to the accompanying drawings, which form a part of the Detailed Description. The Detailed Description should be read with reference to the drawings. The drawings show, by way of illustration, specific embodiments in which the present guide extension catheters and related methods can be practiced. These embodiments are also referred to herein as "examples."

Certain terms are used throughout this patent document to refer to particular features or components. As one skilled in the art will appreciate, different people may refer to the same feature or component by different names. This patent document does not intend to distinguish between components or features that differ in name but not in function. For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" refers to a range of numbers that one of skill in the art considers equivalent to the recited value (i.e., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to an operating physician. "Distal" and "distally" refer to a position that is distant from, or in a direction away from, the physician. "Proximal" and "proximally" refer to a position that is near, or in a direction toward, the physician. And the term "interventional device (s)" is used to include, but is not limited to, guidewires, balloon catheters, stents and stent catheters.

The scope of the present guide extension catheters and methods should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A method comprising:

introducing a guide catheter in vasculature of a patient, wherein the guide catheter extends from a guide catheter proximal end to a guide catheter distal end and defines a guide catheter lumen;

introducing a guide extension catheter in the guide catheter lumen at the guide catheter proximal end, wherein the guide extension catheter comprises:

an elongate tube member having a longitudinal axis and extending from a proximal end to a distal end and defining a guide extension catheter lumen;

a push member mechanically coupled to the proximal end of the elongate tube member;

a concave track coupled to the elongate tube member and the push member, the concave track accessible from a longitudinal side defined transverse to the longitudinal axis of the elongate tube member and defining a partially cylindrical opening and a variable degree of enclosure relative to the longitudinal axis along a length of the concave track leading into the elongate tube member, wherein the concave track comprises a proximal track portion, an intermediary track portion, and a distal track portion, wherein the intermediary track portion defines a smaller degree of enclosure around the longitudinal axis than the distal track portion and the proximal track portion such that the concave track transitions, proximally to distally, from more enclosed to less enclosed, then back to more enclosed before reaching the proximal end of the elongate tube member;

and a manipulation member slidably disposed about an outer perimeter of the push member, wherein the manipulation member is controllably engageable with the push member, wherein, when the manipulation member is in an engaged state with the push member, the manipulation member transmits an axial force to the push member to enable the push member to transmit the axial force to the elongate tube member, and wherein, when the manipulation member is in a disengaged state with the push member, the manipulation member is movable axially in at least one direction along a length of the push member while transmitting substantially no axial force to the push member;

while the manipulation member is in the engaged state with the push member, applying a distal axial force to the manipulation member to advance the guide extension catheter distally within the guide catheter lumen;

disengaging the manipulation member from the push member;

repositioning the manipulation member along the length of the push member;

engaging the manipulation member with the push member; and while the manipulation member is in the engaged state with the push member, applying a distal axial force to the manipulation member to further advance the guide extension catheter distally through the guide catheter lumen.

2. The method of claim 1, wherein the push member is eccentrically coupled to the proximal end of the elongate tube member.

3. The method of claim 1, wherein introducing the guide extension catheter in the guide catheter lumen includes introducing the elongate tube member including a distal portion having a first diameter, a proximal portion having a second diameter that is larger than the first diameter and smaller than a diameter of the guide catheter lumen, and a tapered portion positioned between the distal portion and the proximal portion.

4. The method of claim 1, further comprising advancing a balloon catheter, a stent, or a stent catheter through the guide catheter and the guide extension catheter and into a coronary artery of the patient.

5. The method of claim 1, wherein the manipulation member comprising a tab that defines a hole through which the push member is urged during insertion of the guide extension catheter through the guide catheter.

6. A method comprising:

introducing a guide catheter in vasculature of a patient, wherein the guide catheter extends from a guide catheter proximal end to a guide catheter distal end and defines a guide catheter lumen; and introducing a guide extension catheter in the guide catheter lumen at the guide catheter proximal end, wherein the guide extension catheter comprises an elongate tube member having a longitudinal axis and extending from a proximal end to a distal end and defining a guide extension catheter lumen, a concave track mechanically coupled to the proximal end of the elongate tube member, a push member coupled to the concave track, and a manipulation member slidably disposed about an outer perimeter of the push member, wherein the concave track is accessible from a longitudinal side defined transverse to the longitudinal axis of the elongate tube member and defines a partially cylindrical opening and a variable degree of enclosure relative to the longitudinal axis along a length of the concave track leading into the elongate tube member, wherein the concave track comprises a proximal track portion, an intermediary track portion, and a distal track portion, wherein the intermediary track portion defines a smaller degree of enclosure around the longitudinal axis than the distal track portion and the proximal track portion such that the concave track transitions, proximally to distally, from more enclosed to less enclosed, then back to more enclosed before reaching the proximal end of the elongate tube member, wherein the push member includes a plurality of segments, each of the plurality of segments having a different shape in cross-section, wherein a first segment of the plurality of segments of the push member has a first shape in cross-section defined by a first arcuate surface, the first arcuate surface configured to engage an inner wall surface of the guide catheter along an arch length of the inner wall surface, wherein the manipulation member is controllably engageable with the push member along each of the plurality of segments, wherein, when the manipulation member is in an engaged state with the push member the manipulation member transmits an axial force to the push member to enable the push member to transmit the axial force to the elongate tube member, and wherein when the manipulation member is in a disengaged state with the push member, the manipulation member is movable axially in at least one direction along a length of the push member while transmitting substantially no axial force to the push member.

7. The method of claim 6, further comprising:

while the manipulation member is in the engaged state with the push member, applying a distal axial force to the manipulation member to advance the guide extension catheter distally within the guide catheter lumen;

disengaging the manipulation member from the push member;

repositioning the manipulation member along the length of the push member;

engaging the manipulation member with the push member; and while the manipulation member is in the engaged state with the push member, applying a distal axial force to the manipulation member to further advance the guide extension catheter through the guide catheter lumen.

8. The method of claim 7, further comprising advancing a balloon catheter, a stent, or a stent catheter through the guide catheter and the guide extension catheter and into a coronary artery of the patient.

9. The method of claim 6, wherein a second segment of the plurality of segments of the push member has a second shape in cross-section defined by three arcuate surfaces and one flat surface.

10. The method of claim 6, wherein a third segment of the plurality of segments of the push member has a third shape in cross-section defined that is a rectangle.

11. The method of claim 6, wherein the manipulation member comprising a tab that defines a hole through which the push member is urged during insertion of the guide extension catheter through the guide catheter.

12. A method comprising:

introducing a guide catheter in vasculature of a patient, wherein the guide catheter extends from a guide catheter proximal end to a guide catheter distal end and defines a guide catheter lumen; and introducing a guide extension catheter in the guide catheter lumen at the guide catheter proximal end, wherein the guide extension catheter comprises;

an elongate tube member having a longitudinal axis and extending from a proximal end to a distal end and defining a guide extension catheter lumen, and three portions, each portion having a distinct diameter, wherein a distal portion has a first diameter, a proximal portion has a second diameter which is larger than the first diameter but smaller than a lumen of the guide catheter, and a tapered portion, positioned between the distal portion and the proximal portion, has a variable diameter;

a concave track coupled to the proximal portion of the elongate tube member, the concave track accessible from a longitudinal side defined transverse to the longitudinal axis of the elongate tube member and defining a partially cylindrical opening and a variable degree of enclosure relative to the longitudinal axis along a length of the concave track leading into the elongate tube member, wherein the concave track comprises a proximal track portion, an intermediary track portion, and a distal track portion, wherein the intermediary track portion defines a smaller degree of enclosure around the longitudinal axis than the distal track portion and the proximal track portion such that the concave track transitions, proximally to distally, from more enclosed to less enclosed, then back to more enclosed before reaching the proximal end of the elongate tube member;

a push member mechanically coupled to the proximal track portion, wherein the push member includes a plurality of segments, each of the plurality of segments having a different shape in cross-section, wherein a first segment of the plurality of segments of the push member has a first shape in cross-section defined by a first arcuate surface, the first arcuate surface configured to engage an inner wall surface of the guide catheter along an arch length of the inner wall surface; and a manipulation member slidably disposed about an outer perimeter of the push member, wherein the manipulation member is controllably engageable with the push member along each of the plurality of segments, wherein, when the manipulation member is in an engaged state with the push member the manipulation member transmits an axial force to the push member to enable the push member to transmit the axial force to the elongate tube member, and wherein when the manipulation member is in a disengaged state with the push member, the manipulation member is movable axially in at least one direction along a length of the push member while transmitting substantially no axial force to the push member.

13. The method of claim 12, further comprising:

while the manipulation member is in the engaged state with the push member, applying a distal axial force to the manipulation member to advance the guide extension catheter distally within the guide catheter lumen;

disengaging the manipulation member from the push member;

repositioning the manipulation member along the length of the push member;

engaging the manipulation member with the push member; and while the manipulation member is in the engaged state with the push member, applying a distal axial force to the manipulation member to further advance the guide extension catheter distally through the guide catheter lumen.

14. The method of claim 13, further comprising advancing a balloon catheter, a stent, or a stent catheter through the guide catheter and the guide extension catheter and into a coronary artery of the patient.

15. The method of claim 13, wherein applying a distal axial force to the manipulation member to further advance the guide extension catheter distally through the guide catheter lumen further comprises advancing the guide extension catheter to a position wherein the distal portion of the elongate tube member extends beyond the distal end of the guide catheter while the proximal portion of the elongate tube member remains positioned with the guide catheter lumen.

16. The method of claim 12, wherein the manipulation member comprising a tab that defines a hole through which the push member is urged during insertion of the guide extension catheter through the guide catheter.

* * * * *